United States Patent [19]

Lord

[11] Patent Number: 4,692,518

[45] Date of Patent: Sep. 8, 1987

[54] CRYSTALLINE (7R)-7-AMINO-3-(1'-PYRIDINIUMMETHYL)-3-CEPHEM-4-CARBOXYLATE MONOHYDRATE COMPOUND

[75] Inventor: Gary E. Lord, West Lafayette, Ind.

[73] Assignee: Eli Lilly and Company, Indianapolis, Ind.

[21] Appl. No.: 795,568

[22] Filed: Nov. 6, 1985

[51] Int. Cl.$^4$ .................. C07D 501/38; A61K 31/44
[52] U.S. Cl. .................................. 540/224; 540/225; 548/192; 548/194
[58] Field of Search ........................ 544/25; 540/224

[56] References Cited

U.S. PATENT DOCUMENTS

| | | | |
|---|---|---|---|
| 3,207,755 | 9/1965 | Abraham et al. | 260/243 |
| 4,258,041 | 3/1981 | O'Callaghan et al. | 424/246 |
| 4,369,313 | 1/1983 | Jones et al. | 544/24 |
| 4,374,983 | 2/1983 | Robinson | 544/24 |
| 4,540,779 | 9/1985 | Conrad et al. | 544/24 |

FOREIGN PATENT DOCUMENTS 2052490A  1/1981  United Kingdom .

*Primary Examiner*—Nicholas S. Rizzo
*Attorney, Agent, or Firm*—Paul C. Steinhardt; Leroy Whitaker

[57] ABSTRACT

Crystalline (7R)-7-amino-3-(1'-pyridiniummethyl)-3-cephem-4-carboxylate monohydrate compound is an intermediate in the synthesis of the cephalosporin antibiotic ceftazidime.

1 Claim, No Drawings

CRYSTALLINE (7R)-7-AMINO-3-(1'-PYRIDINIUMMETHYL)-3-CEPHEM-4-CARBOXYLATE MONOHYDRATE COMPOUND

SUMMARY

The present invention encompasses an intermediate in the synthesis of the cephalosporin antibiotic (7)-7-[2-(2'-amino-1',3'-thiazol-4-yl-2-(Z)-[("-carboxyprop-"-oxy)imino]acetamido]-3-(1'-pyridiniummethyl)-3-cephem-4-carboxylate, also known as ceftazidime, which is represented in Formula 1

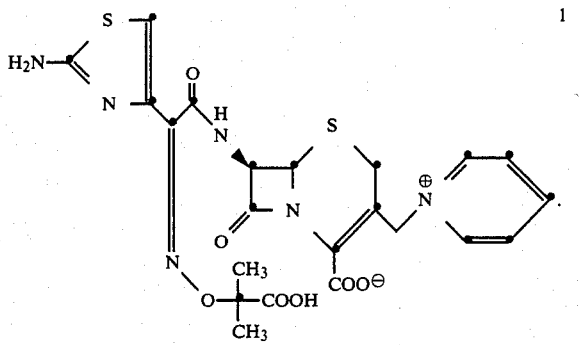

Ceftazidime is described in O'Callaghan et el., U.S. Pat. No. 4,258,041, issued March 24, 1981. The antibiotic possesses excellent activity against a broad spectrum of both gram-positive and gram-negative pathogens.

In the production of an important antiobiotic such as ceftazidime, it is advantageous to have synthetic intermediates that are readily made in a highly pure crystalline salt form which are stable under inexpensive storage conditions for long periods of time.

The instant invention provides such a crystalline, highly stable synthetic intermediate for the production of ceftazidime, namely the crystalline monohydrate form of (7R)-7-amino-3-(1'-pyridiniummethyl)-3-cephem-4-carboxylate.

DETAILED DESCRIPTION

The invention encompasses the crystalline monohydrate form of the compound (7R)-7-amino-3-(1'-pyridiniummethyl)-3-cephem-4-carboxylate, which compound is represented by the following Formula 2:

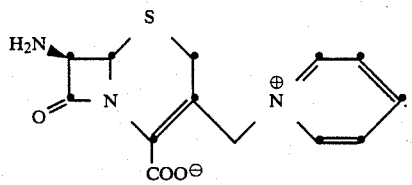

The crystalline monohydrate form of the compound of Formula 2 (hereinafter referred to as the "monohydrate compound") is a white microcrystalline solid which is characterized by its X-ray powder diffraction pattern listed in Table 1 below. The diffraction pattern was obtained with nickel-filtered copper radiation (Cu:Ni) of wavelength =1.5418 angstroms. The interplanar spacings are in the column headed by "d" and the relative intensities in the column "$I/I_1$". (The abbreviation "b" stands for "broad").

TABLE 1

| d | $I/I_1$ |
| --- | --- |
| 10.49 | .06 |
| 7.85 | .32 |
| 7.27 | .06 |
| 6.93 | .24 b |
| 6.14 | .30 |
| 5.33 | .20 |
| 5.00 | .56 |
| 4.79 | .12 |
| 4.30 | 1.00 |
| 4.03 | .28 |
| 3.92 | .14 |
| 3.85 | .14 |
| 3.62 | .82 |
| 3.50 | .60 |
| 3.37 | .26 |
| 3.16 | .08 |
| 3.09 | .02 |
| 3.03 | .08 |
| 2.95 | .02 |
| 2.83 | .06 b |
| 2.66 | .26 |
| 2.61 | .06 b |
| 2.49 | .20 |
| 2.42 | .06 |
| 2.35 | .02 |
| 2.27 | .12 |
| 2.15 | .12 |
| 2.09 | .14 |
| 1.927 | .02 |
| 1.891 | .02 |
| 1.874 | .02 |

The monohydrate compound is made by suspending the dihydrochloride dihydrate form of the compound represented by Formula 2 (hereinafter referred to as the "dihydrochloride dihydrate compound") in an ethanol/methylene chloride solvent system, cooling the resultant suspension, then adding triethylamine. While various mixtures of ethanol and methylene chloride are acceptable, a 1:1 (v:v) ethanol/methylene chloride solvent system is preferred. The preparation can be carried out at a temperature between −40° C. to about 0° C. The resultant crystals of monohydrate compound are isolated by filtration and are dried in vacuo at a temperature between about 25° C. to about 40° C.

The starting material in the synthesis of the instant monohydrate compound, the corresponding dihydrate dihydrochloride compound, is made by cleaving the side chain of (7R)-7-(2-(thien-2'-yl)acetamido)-3-(1'-pyridiniummethyl)-3-cephem-4-carboxylate, also known as "cephaloridine". The side chain is cleaved by first silylating cephaloridine, treating the silylated derivative with phosphorous pentachloride, and finally adding isopropanol or butanediol. The precipitate of deacylated (7R)-7-amino product thus obtained is dissolved in hydrochloric acid and the dihydrochloride dihydrate compound is precipitated by the addition of isopropanol to the acidic solution.

An experimental procedure of the above synthesis of the dihydrochloride dihydrate compound is given in Preparation 10 (column 17) of O'Callaghan et al., U.S. Pat. No. 4,258,041, issued March 24, 1981, which is herein incorporated by reference in its entirety.

As discussed above, the monohydrate compound of the instant invention is an intermediate in the synthesis of the antibiotic ceftazidime, represented by the above Formula 1. In the synthesis, the monohydrate compound is acylated with the acid chloride form of the compound represented by the following Formula 3

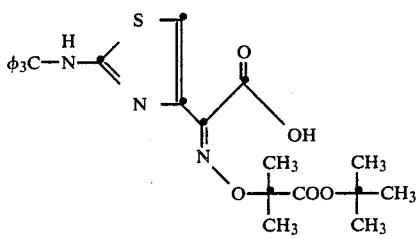

The compound of Formula 3, 2-((2'-tritylamino)-1', 3'-thiazol-4'-yl)-2-(Z)-[(2''-(t-butyl carboxylate)prop-2''-oxy)imino]acetic acid, is converted to the corresponding acid chloride with phosphorous pentachloride. The acylation reaction yields (7R)-7- [2'-(2''-(tritylamino)-1'',3''-thiazol-4''-yl)-2'- (Z)-[((2''-(t-butyl carboxylate)- prop-2''-oxy)imino)-acetamido]-3-(1'-pyridiniumme- thyl)-3-cephem-4-carboxylate, referred to hereinafter as "blocked ceftazidime". The blocked ceftazidime compound is treated sequentially with concentrated formic acid and concentrated hydrochloric acid to remove the protecting groups and give ceftazidime (Formula 1 above) as the dihydrochloride form.

The conversion of the compound of Formula 3 to blocked ceftazidime is further discussed below in the Experimental Section. The conversion of blocked ceftazidime to the dihydrochloride form of ceftazidime is discussed in O'Callaghan et al., U.S. Patent No. 4,258,041, especially in columns 23 and 24.

EXPERIMENTAL SECTION

In the following experimental section, the infrared spectra were taken on a Perkin-Elmer Model 681 instrument. The nuclear magnetic resonance spectra were taken at 60 MHz on a Varian Associates T-60 instrument.

In the following discussion, the abbreviations "mmol", "v:v", "i.r.", and "n.m.r." stand for millimole, volume to volume, infrared spectrum, and nuclear magnetic resonance spectrum, respectively. With respect to the nuclear magnetic resonance spectra, the abbreviations "d", "s", and "m" stand for doublet, singlet, and multiplet, respectively. The n.m.r. absorbances are expressed in delta units relative to DSS (sodium 3-(trimethylsilyl)propylsulfonate). In addition, the absorbances listed for the infrared spectrum are only those of interest and not all of the maxima observed.

The following Preparation and Example are provided to further illustrate the invention. It is not intended that the invention be limited in scope by reason of any of the following Preparation or Example.

PREPARATION 1

(7R)-7-[2'-(2''-(Tritylamino)-1'',3''-Thiazol-4''-yl)-2'-(Z)-[((2''-(t-Butyl Carboxylate)prop-2''-oxy)imino)acetamido]-3-(1'-Pyridiniummethyl)-3-Cephem-4-Carboxylate Denatured alcohol (12 ml), dichloromethane (12 ml) and (7R)-7-amino-3-(1'-pyridiniummethyl)-3-cephem-4-carboxylate monohydrate (1.53 g) were combined and the solution was cooled to −15°C. In another vessel, (2-((2'-tritylamino)- 1',3'-thiazol-4'-yl)-2-(Z)-[(2''-(t-butyl carboxylate)prop-2''-oxy)imino]acetyl chloride was prepared by first stirring phosphorus pentachloride (1.45 g) and dichloromethane (20 ml) at room temperature for 20 minutes. The solution was cooled to −15° C. and the corresponding carboxylic acid derivative (Formula 3, 3.47 g) was added. This mixture was stirred for 20 minutes then a solution of triethylamine (1.53 g) in water (14 ml, 0° C.) was added. The layers were separated and the organic layer was held briefly. To the slurry containing the monohydrate compound was added triethylamine (2.00 ml) followed by the organic layer of the acid chloride. The resultant mixture was stirred for 1 hour at 0° C. The mixture was combined with water (54 ml), the layers were separated, and the lower organic layer was combined with ethyl acetate (40 ml), ether (20 ml), and N,N-dimethylacetamide (20 ml). The resultant crystalline precipitate was a 77.7% yield of (7R)-7-[2'-(2''-(tritylamino)-1'', 3''-thiazol-4''-1)-2'-(Z)-[((2''-(t-butyl carboxylate)- prop-2''-oxy)imino)acetamido]3-(1'-pyridiniummethyl)-3- cephem-4-carboxylate.

EXAMPLE 1

(7R)-7-Amino-3-(1'-Pyridiniummethyl)-3-Cephem-4-Carboxylate Monohydrate (7R)-7-Amino-3-(1'-pyridiniummethyl)-3-cephem-4-carboxylate dihydrochloride dihydrate (62.71 g, 68.0%, 146.4 mmol) was slurried in a 3A alcohol/methylene chloride (365 ml/363 ml) mixture and the slurry was cooled to −40° C. Triethylamine (88.89 g, 878.4 mmol) was added over seven minutes, a precipitate formed and the mixture was stirred for an additional 7 hours. During that period the mixture was warmed from −33° C. to 0° C. The mixture was filtered (at −7° C.) then washed with a solution of 10% 3A ethanol in methylene chloride (40 ml). The collected precipitate was dried in vacuo overnight at room temperature to give 44.15 g, 93.4% yield of (7R)-7-amino-3-(1'-pyridinium- methyl)-3-cephem-4-carboxylate monohydrate: n.m.r. (D$_2$O, 60 MHz), δ3.18 (d, J=18, one of the C-2 methylene protons), 3.68 (d, J=18, one of the C-2 methylene protons), 4.65 (s, water), 4.85 and 5.13 (each d, C-6 and C-7 protons), 5.33 and 5.66 (each d, 1'-methylene protons), 8.20 (m, beta protons on pyridinium ring), 8.68 (m, gamma protons on pyridinium ring), 9.05 (m, alpha protons on pyridinium ring); i.r. (KBr): 1774, 1606 cm$^{-1}$.

I claim:

1. The crystalline monohydrate of 7-(R)-amino-3-(1-pyridiniummethyl)-3-cephem-4-carboxylate which has the following X-ray powder diffraction obtained with nickel-filtered copper radiation of λ=1.5418 angstroms, wherein d represents the interplanar spacing and I/I$_1$ the relative intensity:

| d | I/I$_1$ |
| --- | --- |
| 10.49 | .06 |
| 7.85 | .32 |
| 7.27 | .06 |
| 6.93 | .24 b |
| 6.14 | .30 |
| 5.33 | .20 |
| 5.00 | .56 |
| 4.79 | .12 |
| 4.30 | 1.00 |
| 4.03 | .28 |
| 3.92 | .14 |
| 3.85 | .14 |
| 3.62 | .82 |
| 3.50 | .60 |
| 3.37 | .26 |
| 3.16 | .08 |
| 3.09 | .02 |

-continued

| d | I/I$_1$ |
|---|---|
| 3.03 | .08 |
| 2.95 | .02 |
| 2.83 | .06 b |
| 2.66 | .26 |
| 2.61 | .06 b |
| 2.49 | .20 |

-continued

| d | I/I$_1$ |
|---|---|
| 2.42 | .06 |
| 2.35 | .02 |
| 2.27 | .12 |
| 2.15 | .12 |
| 2.09 | .14 |
| 1.927 | .02 |
| 1.891 | .02 |
| 1.874 | .02. |

* * * * *